United States Patent [19]

O'Leary et al.

[11] Patent Number: 5,405,390
[45] Date of Patent: Apr. 11, 1995

[54] OSTEOGENIC COMPOSITION AND IMPLANT CONTAINING SAME

[75] Inventors: Robert K. O'Leary, Spring Lake; Annamarie B. Prewett, Little Silver, both of N.J.

[73] Assignee: Osteotech, Inc., Shrewsbury, N.J.

[21] Appl. No.: 71,449

[22] Filed: Jun. 2, 1993

Related U.S. Application Data

[60] Division of Ser. No. 642,633, Jan. 17, 1991, Pat. No. 5,236,456, which is a continuation-in-part of Ser. No. 434,937, Nov. 9, 1989, abandoned.

[51] Int. Cl.⁶ ............................................. A61F 2/28
[52] U.S. Cl. .................................................. 623/16
[58] Field of Search ........................................ 623/16

[56] References Cited

U.S. PATENT DOCUMENTS

| | | |
|---|---|---|
| 2,968,593 | 1/1981 | Rapkin . |
| 4,394,370 | 7/1983 | Jefferies ............... 424/15 |
| 4,440,750 | 4/1984 | Glowacki et al. ......... 424/95 |
| 4,472,840 | 9/1984 | Jefferies ............... 623/16 |
| 4,485,097 | 11/1984 | Bell . |
| 4,516,276 | 5/1985 | Mittelmeier et al. ...... 623/18 |
| 4,563,350 | 1/1986 | Nathan et al. . |
| 4,581,030 | 4/1986 | Bruns et al. ........... 128/DIG. 8 |
| 4,789,732 | 12/1988 | Urist .................. 623/16 |
| 4,824,939 | 4/1989 | Simpson . |
| 4,888,366 | 12/1989 | Chu et al. ............. 623/16 |
| 4,975,526 | 12/1990 | Kuberasampath et al. ... 128/DIG. 8 |
| 5,053,049 | 10/1991 | Campbell . |
| 5,073,373 | 12/1991 | O'Leary et al. ......... 623/16 |

FOREIGN PATENT DOCUMENTS

| | | |
|---|---|---|
| 321442A3 | 6/1989 | European Pat. Off. . |
| 366029A3 | 5/1990 | European Pat. Off. . |
| 419275A1 | 3/1991 | European Pat. Off. . |
| WO8911880 | 12/1989 | WIPO . |

OTHER PUBLICATIONS

Kakiuchi, et al., "Human Bone Matrix Gelatin As A Clinical Alloimplant", International Orthopaedics, vol. 9, pp. 181–188 (1985).

McLaughlin, et al., "Enhancement of Bone Ingrowth By The Use Of Bone Matrix As A Biologic Cement", Clinical Orthopaedics Related Research, No. 183, pp. 255–261 (Mar. 1984).

Todescan, et al., "A Small Animal Model For Investigating Endosseous Dental Implants: Effect of Graft Material on Healing of Endosseous, Porous–Surfaced Implants Placed in a Fresh Extraction Socket", The International Journal of Oral & Maxillofacial Implants, vol. 2, No. 4, p. 217–223 (1987).

Primary Examiner—Randall L. Green
Assistant Examiner—Rob Clarke
Attorney, Agent, or Firm—Dilworth & Barrese

[57] ABSTRACT

An osteogenic composition is obtained from demineralized bone tissue.

32 Claims, 1 Drawing Sheet

OSTEOGENIC COMPOSITION AND IMPLANT CONTAINING SAME

CROSS-REFERENCE TO RELATED APPLICATION

This is a divisional of application Ser. No. 07/642,633 filed Jan. 17, 1991, now U.S. Pat. No. 5,236,456, which is a continuation-in-part of commonly assigned U.S. patent application Ser. No. 07/434,937, filed Nov. 9, 1989 now abandoned.

BACKGROUND OF THE INVENTION

This invention relates to a material exhibiting osteogenic activity and, more particularly, to a surface-adherent osteogenic composition derived from demineralized bone. The invention further relates to a natural or synthetic implant, e.g., allograft bone tissue or an osteoprosthetic device, which is coated with or otherwise contains the osteogenic composition.

The use of pulverized exogenous bone growth material, e.g., derived from demineralized allogenic or xenogeneic bone in the surgical repair or reconstruction of defective or diseased bone is known. See, in this regard, the disclosures of U.S. Pat. Nos. 4,394,370; 4,440,750; 4,472,840; 4,485,097; 4,678,470; and, 4,743,259; Bolander et al., "The Use of Demineralized Bone Matrix in the Repair of Segmental Defects", *The Journal of Bone and Joint Surgery*, Vol. 68-A, No. 8, pp. 1264–1273; Glowacki et al., "Demineralized Bone Implants", *Symposium on Horizons in Plastic Surgery*, Vol. 12, No. 2, pp. 233–241 (1985); Gepstein et al., "Bridging Large Defects in Bone by Demineralized Bone Matrix in the Form of a Powder", *The Journal of Bone and Joint Surgery*, Vol. 69-A, No. 7, pp. 984–991 (1987); Mellonig, "Decalcified Freeze-Dried Bone Allograft as an Implant Material In Human Periodontal Defects", *The International Journal of Periodontics and Restorative Dentistry*, pp. 41–45 (June, 1984); Kaban et al., "Treatment of Jaw Defects with Demineralized Bone Implants", *Journal of Oral and Maxillofacial Surgery*; and, Todescan et al., "A Small Animal Model for Investigating Endosseous Dental Implants: Effect of Graft Materials on Healing of Endosseous, Porous-Surfaced Implants Placed in a Fresh Extraction Socket", *The International Journal of Oral & Maxillofacial Implants*, Vol. 2, No. 4, pp. 217–223 (1987). According to Kakincki et al., "Human bone matrix gelatin as a clinical alloimplant", *International Orthopaedics*, 9, pp 181–188 (1985), a water insoluble osteogenic substance referred to therein as "bone matrix gelatin" which was obtained by decalcifying (i.e., demineralizing) bone was successfully employed as an alloimplant for the treatment of bone defects and other disorders. An apparently similar water insoluble osteogenic material, referred to as "decalcified bone matrix", is disclosed in McLaughlin et al, "Enhancement of Bone Ingrowth by the Use of Bone Matrix as a Biologic Cement", *Clinical Orthopaedics and Related Research*, No. 183, pp. 255–261 (March, 1984).

SUMMARY OF THE INVENTION

It is a principal object of the invention to provide a surface-adherent osteogenic composition derived from autogenic, allogeneic or xenogeneic bone.

It is also an object of the invention to provide a natural or synthetic implant containing a new bone growth-inducing component, e.g., in the form of a coating applied to a surface thereof, which is derived from demineralized and thermally modified bone tissue.

It is an additional object of the invention to provide a method for obtaining the foregoing osteogenic composition.

It is another object of the invention to provide a surface-adherent osteogenic composition derived from autogenic, allogeneic or xenogeneic bone and which is liquid, preferably in a viscous liquid state.

It is a further object of the invention to provide an osteogenic composition derived from autogenic, allogeneic or xenogeneic bone and which is suitable for injection into tissue, e.g., into a bone implant site.

In keeping with these and other objects of the invention, there is provided an osteogenic composition resulting from the process comprising:

a) demineralizing bone tissue to provide a demineralized bone matrix from which at least a substantial portion of the original calcium content of the tissue has been removed, said matrix being made up of acid insoluble collagenous residue and non-collagenous proteinaceous matter;

b) subjecting the demineralized bone matrix to acid-promoted cleavage of intra-molecular bonds in collagen molecules and inter-molecular bonds between collagen molecules to provide a cleavage product which is acid soluble upon heating; and, c) heating the cleavage product to provide a liquid surface-adherent osteogenic composition.

More specifically, the surface-adherent osteogenic composition prepared in step (c) is in viscous liquid form and will remain in this viscous form if kept in a sealed container, even after the temperature in heating step (c) is lowered.

Due to its ability to tenaciously adhere to solid or rigid surfaces, the foregoing osteogenic composition when applied to a bone implant, for example donor osseous tissue, an osteoprosthetic device, and the like, imparts a significant new bone growth-inducing capability to the implant. The foregoing osteogenic composition can be treated in an additional step (d) to obtain the osteogenic composition in solid form. For example, the osteogenic composition produced in step (c) can be optionally titrated to remove excess acid and then organic solvent can be added, whereby the osteogenic composition precipitates out of solution in solid form, e.g., as a powder. This solid form of the osteogenic composition can then be separated from the organic solvent and subsequently treated, e.g. by lyophilization and resolubilization, so that the osteogenic composition is in suitable form for injection, e.g. into a bone implant site.

The solid form of the osteogenic composition can also be obtained by placing the viscous liquid composition, which has been titrated to an appropriate pH, in a cellulose dialysis bag, with the resulting salts removed by dialysis. The powder is then obtained following lyophilization. Furthermore, the acid-promoted cleavage in step (b) can be carried out simultaneously with the bone demineralization in step (a) or can be carried out separately after the bone demineralizing step (a) has been completed. Moreover, the heating step (c) can be carried out simultaneously with or subsequent to the acid-promoted cleavage of step (b).

In addition, the osteogenic composition herein is compatible with many types of materials which can be introduced in the composition to further enhance or augment bone repair or reconstruction. Thus the invention contemplates the addition of demineralized bone powder and other osteogenic, osteoinductive and/or osteoconductive substances such as bone morphogenic proteins (BMP) and/or any of numerous other medically useful substances to the osteogenic composition.

DESCRIPTION OF THE PREFERRED EMBODIMENTS

Figure 1:
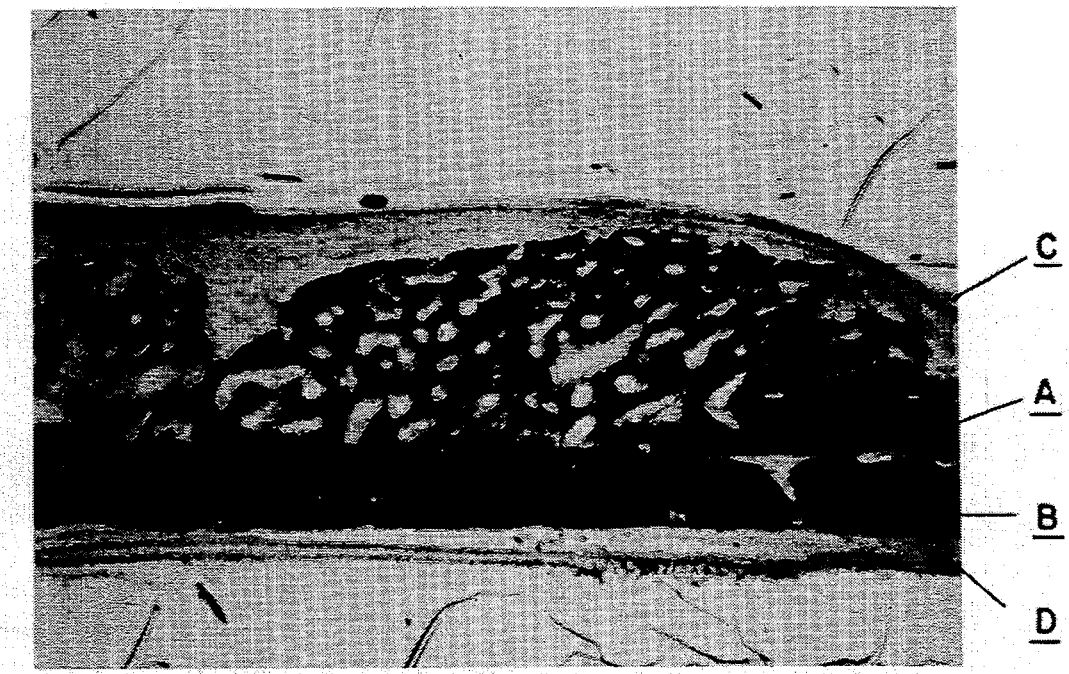
FIG. 1 is a photomicrograph (12½ times magnification) of a section of living tissue treated with the osteogenic composition of the present invention; and, FIG. 2 is a photomicrograph (12½ times magnification) of a section of living tissue treated with a control composition.

The starting material, or source, for the osteogenic composition of this invention is cortical, cancellous and/or corticocancellous autogenic, allogeneic or xenogeneic bone. The bone is first subjected to an acid demineralizing operation, preferably one that exhaustively removes calcium from the tissue.

The initial bone demineralization operation can be carried out in accordance with known techniques, e.g., as described in Reddi et al, . "Biochemical sequences in the transformation of normal fibroblasts in adolescent rats", *Proc. Nat. Acad. Sci.*, 69 pp. 1601–5 (1972), the contents of which are incorporated by reference herein. In a preferred bone demineralization procedure, the bone is first pulverized to the desired average particle size followed by defatting/disinfecting and acid demineralization treatments. A preferred defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10% to 40% water (i.e., about 60% to 90% defatting agent such as alcohol) should be present in the defatting, disinfecting solution to produce optimal lipid removal and disinfection within the shortest period of time. The preferred concentration range of the defatting solution is about 60% to 85% alcohol and most preferably about 70% alcohol.

Following defatting, the bone is immersed in acid or chelating agent over time to effect demineralization. Acids which can be employed in this operation include inorganic acids such as hydrochloric acid and organic acids such as peracetic acid, and chelating agents include disodium ethylenediaminetetraacetic acid (Na₂EDTA). The concentration of the acid or chelating agent in such demineralization operation is generally about 0.5N to about 1.0N, with demineralizing time being from about 2 to about 2 hours under ambient conditions.

It is preferred that essentially all of the original calcium content of the bone be removed in the demineralization procedure. For example, it is advantageous that the demineralized bone contain no greater than about 10, preferably no greater than about 1 and most preferably no greater than about 0.5 weight percent calcium. This demineralization treatment provides insoluble collagenous residue and associated non-collagenous proteinaceous matter which together constitute a demineralized bone matrix.

After the demineralization operation has been completed, the bone tissue is then subjected to a separate acid-promoted treatment either accompanied with, or followed by, heating to provide the osteogenic composition of this invention. Generally, following the demineralization step and before the acid-promoted cleavage step, the acidic solution containing calcium phosphates generated in the demineralization is removed by allowing particles constituting the demineralized bone matrix to settle followed by decantation of the solution. However, the demineralization step and the acid-promoted cleavage step can be accomplished synchronously by utilizing a high concentration of acid throughout these process steps. For example, instead of demineralizing in about 0.6N HCl, the bone tissue can be placed in a solution containing about 2N HCl or greater concentration for a period of time sufficient both to demineralize the bone and to also carry out the acid-promoted cleavage treatment.

The acid-promoted cleavage of intra-molecular bonds in collagen molecules and inter-molecular bonds between collagen molecules in the demineralized bone matrix provides a cleavage product which is acid soluble upon heating. While the acid-promoted cleavage treatment of the demineralized bone can utilize the same acid as used in the demineralization step, acid concentration will generally be greater at least to the point where the acid will effectively disrupt protein-protein ionic bonds and perhaps some limited numbers of covalent bonds as well. For example, in the case of hydrochloric acid, a concentration of at least about 2.0N will usually provide good results. Minimum concentrations for other acids can be readily determined using simple and routine testing. The concentration of the acid during the acid-promoted cleavage treatment is generally about 2.0N to about 3.0N. Contact time can vary widely, from a few minutes to several hours depending upon temperature and bone tissue particle size or surface area, e.g., preferably about 20 minutes to 30 hours, more preferably about 2 to 24 hours, being sufficient to yield the desired result.

Prior to acid-promoted cleavage treatment, the demineralized bone particles, although softened by the removal of minerals, will be relatively firm and large segments of the demineralized bone will be rigid. However, when a suitable degree of acid-promoted cleavage of bonds has been achieved, the demineralized bone will become relatively soft in character and/or fairly flexible, even rubber-like in behavior, i.e., converted to a pulp. It appears, then, that as a result of the acid-promoted cleavage, the fibrillar structure of the collagen component of the demineralized bone has undergone chemical modification and as such no longer exists in its original fibrillar form. It further appears that covalent modification of both the collagen molecules and other proteins in the bone matrix has been effected. Acid-promoted cleavage of the proteins and the strong acidic conditions to which the bone segments and particles have been subjected, permit the bone matrix particles to undergo a phase change, from solid to liquid, following exposure to heat. Whatever may, in fact, be the mechanism or effect of the acid-promoted treatment, it remains that the thus-heated bone tissue undergoes an alteration of physical state.

The effectiveness of the acid-promoted cleavage step can be judged in terms of the resulting physical change which occurs in the treated bone material during subsequent thermal denaturation. If the acid hydrolysis degradation has been inadequate, then the bone particles will not undergo a phase change into viscous liquid form upon thermal treatment infra.

In order to convert the demineralized and chemically modified bone tissue in the pulp state to the viscous liquid state which is the apparently homogeneous osteogenic composition of this invention, the tissue is heated, preferably to a temperature of from about 30° to about 75° C., more preferably from about 35° to about 60° C. and most preferably from about 40° to about 55° C. until the aforedescribed composition is obtained, a period generally ranging from about 5 minutes to about 10 hours depending on the temperature level. This heating operation can accompany the acid-promoted treatment described above or it can be carried out subsequent to the latter treatment following removal of the acidic solution in which the particles are suspended.

At ambient temperature, e g., below about 25° C. the osteogenic composition of this invention is in viscous liquid form, e.g. having a viscosity such as about 10 to about 16,000 centipoises, and strongly adheres to all manner of solid or rigid surfaces to which it is applied. The viscous liquid can be changed into a gel by cooling much below room temperature, e.g. to about 0°-5° C. The molecular weight range of the osteogenic composition is from about several hundred to about several thousand kilodaltons. The osteogenic composition will remain in viscous liquid form, even after the temperature is lowered, as long as the composition is maintained in a sealed container. If left exposed to ambient air, the liquid phase of the osteogenic composition will eventually evaporate, leaving a solid mass.

The resulting osteogenic composition can, after heating, be further treated so that it is in a different physical state, e.g. in a form suitable for injection into tissue such as a bone implant site. In this regard, the osteogenic composition can be introduced into an organic solvent, whereby soluble constituents of the composition such as HCl and certain organically-soluble proteins, peptides, and lipids are dissolved in solution and insoluble constituents such as the osteogenic proteins, gelatin, and collagen precipitate out as solid material, e.g. powder. This organically insoluble material is then separated from the solution, such as by centrifuging and/or decanting, and can then be reintroduced into organic solvent, if necessary, to remove any remaining organically-soluble constituents therefrom. The organic solvent is again separated from the precipitate, e.g. by centrifuging or decanting.

Alternatively, the viscous osteogenic liquid, which still retains a high concentration of hydrochloric acid (approximately 2.0N) can be titrated with a suitable basic substance such as a solution containing 1.0N sodium hydroxide until a pH of about 3 is obtained. At this pH, the hydrolytic degradation of the proteins caused by the acid is stopped. A suitable organic solvent such as methanol then can be added to the viscous osteogenic solution and soluble materials such as HCl, NaCl formed from the neutralization of acid supra, and certain organically-soluble proteins, peptides, lipids and saccharides can be removed from such insoluble materials as the osteogenic proteins, collagen and gelatin which precipitate in this solvent system.

The separated precipitate can then be lyophilized to yield a dry powder. Such lyophilization can be carried out in accordance with known techniques, e.g. as described in D. Freifelder, *Physical Biochemistry*, W. H. Freeman & Co., San Francisco, page 527, the contents of which are incorporated by reference herein. Alternatively, the viscous osteogenic composition can be first titrated to remove excess acid and then subjected to dialysis, after which the contents remaining in the dialysis bag can be converted to a powder by lyophilization. Suitable dialysis technique which can be applied herein is described at pages 153-158 of Freifelder supra, also incorporated by reference herein.

Then, the thus-lyophilized product, i.e., dry powder of the osteogenic composition of the present invention can be reconstituted, as needed, into a suitable form for injection into tissue. For example, the dry powder can be added to an aqueous solvent including 1% acetic acid or 0.001M HCl to form a solution which is then added to a syringe for injection into tissue. The solution formed for injection preferably comprises about 0.05 to about 2% by weight, more preferably about 0.10 to about 1% by weight, and most preferably about 0.15 to about 0.5% by weight of the dry powder.

The composition, whether in viscous liquid form or in solution for injection, serves as an excellent vehicle or carrier for a host of medically/surgically useful substances including insoluble solids such as demineralized bone powder already mentioned, collagen and insoluble collagen derivatives, hydroxyapatite, etc., and soluble solids and/or liquids dissolved therein, e.g., those suitable for preventing transmission of acquired immune deficiency syndrome (AIDS); antivirals, antimicrobials and/or antibiotics such as erythromycin, bacitracin, neomycin, penicillin, polymyxin B, tetracyclines, vincomycin, chloromycetin and streptomycins, cefazolin, ampicillin, tobramycin, clindamycin and gentamycin, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer-cell scaffolds with parenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, natural extracts, tissue transplants, bioadhesives, biologically active components such as bone morphogenetic proteins (BMPs), transforming growth factor (TGF-beta), insulin-like growth factor (IGF-1); mesenchymal elements; bone digestors; antitumor agents; cellular attractants and attachment agents; immunosuppressants; permeation enhancers, e.g., fatty acid esters such as the laurate, myristate and stearate monoesters of polyethylene glycol, hexamine derivatives, alpha-keto aldehydes, etc.; and nucleic acids.

For example, the osteogenic composition can contain at least one ingredient selected from the group consisting of antiviral agent, antimicrobial agent, antibiotic agent, amino acid, peptide, vitamin, inorganic element, hormone, endocrine tissue, synthesizer, enzyme, polymer-cell scaffolding agent with parenchymal cells, angiogenic drug, polymeric drug carrier, collagen lattice, antigenic agent, cytoskeletal agent, cartilage fragment, living cell, natural extract, tissue transplant, bioadhesive, biologically active component, mesenchymal agent, bone digester, antitumor agent, cellular attractant, cellular attachment agent, immunosuppressant, nucleic acid and penetration enhancer.

Especially preferred additives include hydroxyapatite, demineralized or non-demineralized bone, and bone morphogenic agents or growth factors such as platelet derived growth factor, basic fibroblast growth factor, transforming growth factor beta, insulin-like growth factor, and epidermal growth factor. Especially-preferred penetration enhancers include octoxynol, available as Triton X-100 from Rohm and Haas, Philadelphia, Pa. and also glycerol monolaurate. Preferred polymeric carriers include biological polymers such as collagens, synthetic polymers such as polylactic and glycolic acids, polyvinylpyrrolidones, and polyorthoesters, with methylcellulose, carboxymethylcellulose, hydroxypropylcellulose, and derivatives thereof being especially preferred for the viscous liquid form of the osteogenic composition. The amounts of optionally added substances can vary widely with optimum levels being readily determined in a specific case by routine experimentation.

The soluble materials can be added directly to the osteogenic composition and/or they can be present absorbed within any insoluble particulate additive therein, e.g., within demineralized bone powder. The osteogenic composition of the present invention, whether in viscous liquid or injectable solution form, is soluble in weakly acidic solutions, i.e. solutions having a pH from about 1 to about 5. Thus, when the osteogenic composition is applied to living tissue which generally has a pH of about 7.4, the osteogenic composition will tend to bioerode over time, effectively promoting osteogenesis.

In particular, the osteogenic composition, when in injectable form, is especially suitable for delivery by percutaneous injection to a fracture site, for direct injection into an osseous defect resulting from periodontal disease (sub-gingival injection), or generally as an substance for stimulation of bone growth to counteract bone loss due to injury or disease.

The osteogenic composition of this invention can be applied to a bone defect site in a variety of ways, e.g., by packing the site with the composition provided in the form of a powder or a highly viscous paste or liquid, or by direct injection. In view of its adherency qualities, it is particularly advantageous to apply the osteogenic composition to the surface of bone implants and osteoprosthetic devices where it will exert a new bone growth-inducing effect which tends to hasten or accelerate bone repair or reconstruction. An advantageous feature of the osteogenic composition is its ability to penetrate into a porous matrix or structure. A suitable surgical implant device upon which the osteogenic composition is applied is selected from the group consisting of donor bone tissue, an osteoprosthetic device, an orthopedic fracture wrapping and a collagen-coated microspherical filler.

More particularly, the osteogenic composition with or without one or more of the aforementioned optional ingredients contained therein can be applied to the surface of a bone implant device in any one of several specific ways. Thus, e.g., a surface of the implant can simply be contacted with the freshly prepared osteogenic solution while it is still in acidic viscous liquid condition or the majority of the acidity can be neutralized with a suitable base leaving a saline solution with pH closer to neutrality, e.g. pH about 3 to about 5. Suitable bases include NaOH, KOH and NH4OH. Additionally, sublimable buffers such as ammonium bicarbonate can be employed to reduce acidity. The composition can also be applied to the surface of the implant or permitted to impregnate the implant as an aqueous viscous solution, followed by removal of the solvent to dryness. Moreover, prior to any application, the acidic solvent can be removed and then the dry osteogenic composition can be ground to a powder and applied to the implant as part of a layer of bioerodible or nonbioerodible material, numerous ones of which are known in the art.

The thickness of the coating or layer of osteogenic composition in viscous liquid form on an implant is not especially critical. Average thicknesses of from about 1 to about 50 mils and advantageously from about 10 to about 40 mils generally provide satisfactory results. If desired, the surface of the implant which is to receive the osteogenic coating or layer can be subjected to one or more preparative treatments in order to enhance the adhesion of the osteogenic coating or layer thereto. For example, the surface of the prosthesis can be provided with an adhesion-promoting pattern formed as described in U.S. Pat. No. 4,778,469, or an adhesion-promoting roughened surface texture as described in U.S. Pat. No. 4,159,358.

In particular, prior to application of the osteogenic composition of the present invention, the tissue, i.e. bone, can be etched, e.g. with laser beams. The bone can then be treated with the osteogenic composition in its viscous liquid state. Alternatively, the osteogenic composition, when reconstituted as a powder and rehydrated using a dilute acidic solution, can be injected into tissue such as an intercalary graft destined to be transplanted.

The following examples are illustrative of the osteogenic composition of this invention, its method of preparation and application, including a hip joint prosthesis coated with the composition and demineralized or nondemineralized bone powder distributed therein.

EXAMPLE 1

A. Preparation of Exhaustively Demineralized Cortical Bone Powder

A quantity of cortical bone which has been pulverized and sieved to an average particle size of from about 100 to about 300 microns is introduced into a reactor which is then sealed. A 70% ethanol solution at the rate of 30 milliliters per gram of bone is introduced into the reactor followed by agitation for 1 hour (Bolander et al., *Journal of Bone and Joint Surgery*, Vol. 68-A, No. 8 (October 1986)) to effect defatting and disinfecting of the bone powder. Following drainage of the ethanol, a 0.6N solution of HCl at a rate of 50 ml per gram of bone is introduced into the reactor (Bolander et al., ibid.), the reaction proceeding for 3 hours (Glowackie, AATB Workshop, 11th Annual meeting (1987)). Essentially complete removal of calcium is achieved (less than 0.1 weight percent calcium remains in the bone).

B. Acid-Promoted Cleavage and Thermal Treatment of Exhaustively Demineralized Bone Powder After step (A) has been completed, the acid is decanted, i.e., separated from the bone powder and the demineralized bone powder from preceding step (A) is then subjected to further treatment with a solution of greater acidity to effect cleavage, denaturation, and limited hydrolysis of the proteins. A solution containing 2N to 3N HCl is added to the drained bone powder in a ratio of 15 ml to 1 g. The demineralized bone powder remains in the acidic solution for a time period of 2 hours. Following this treatment, the soft demineralized bone powder is drained free of residual acid solution and placed in a temperature controlled oven whose temperature is fixed in a range of 40° C. to 50° C. Over a period of 30 minutes, the demineralized bone powder undergoes a phase change and achieves a viscous liquid form.

C. Application of the Viscous Liquid Osteogenic Composition

A concentrated acidic solution of the foregoing osteogenic composition is applied as a coating to a hip joint prosthesis and demineralized bone powder is applied thereto while the coating is still tacky. Following drying of the coating, residual acidity is removed by washing the coated prosthesis with 95% ethanol. Residual ethanol is removed by evaporation under vacuum. A prosthesis is obtained in which surfaces thereof possess a layer of demineralized bone powder distributed within a matrix of the osteogenic composition of this invention.

The above application step (C) on a hip joint prosthesis is repeated with non-demineralized bone powder to form a layer of non-demineralized bone powder distributed within a matrix of the osteogenic composition of this invention, and is repeated with just the viscous osteogenic solution alone.

EXAMPLE 2

A. Preparation of the Viscous Osteogenic Composition

Freeze-dried cortical bone chips, size ranging from 0.2 to 1 mm, and weight of 50.60 g are placed into 150 ml of a solution of 0.6N HCl. The chips are stirred at a temperature of 25° C. for 3 hours. The acid is decanted and 750 ml of 10% HCl (2.9M) is added. The chips are incubated in the acidic solution for an additional two hours. The acid is decanted from the bone and the bone chips are placed in a 40° C. oven for 30 minutes. The bone particles liquefy over this time interval. The viscous, syrupy liquid is separated from remaining insolubles by filtration over a coarse, sintered glass filter.

B. Preparation of the Soluble Osteogenic Powder and Subsequent Injectable Solution To the liquefied cortical bone extract is added methanol in a 10:1 v/v ratio. The solution is maintained at 4° C. for one-half hour and the methanol insoluble protein is precipitated. The powder is separated from the solvent by centrifugation at low speed under 3000 g for 15 minutes. The solvent is decanted, the pelleted protein is resuspended in methanol and the centrifugation step is repeated. The pellet is lyophilized to yield a dry powder. The osteogenic powder is resolubilized in a dilute solution of hydrochloric acid (0.001M; pH=3).

C. In Vivo Characterization of the Osteogenic Powder In Solution

Figure 2:
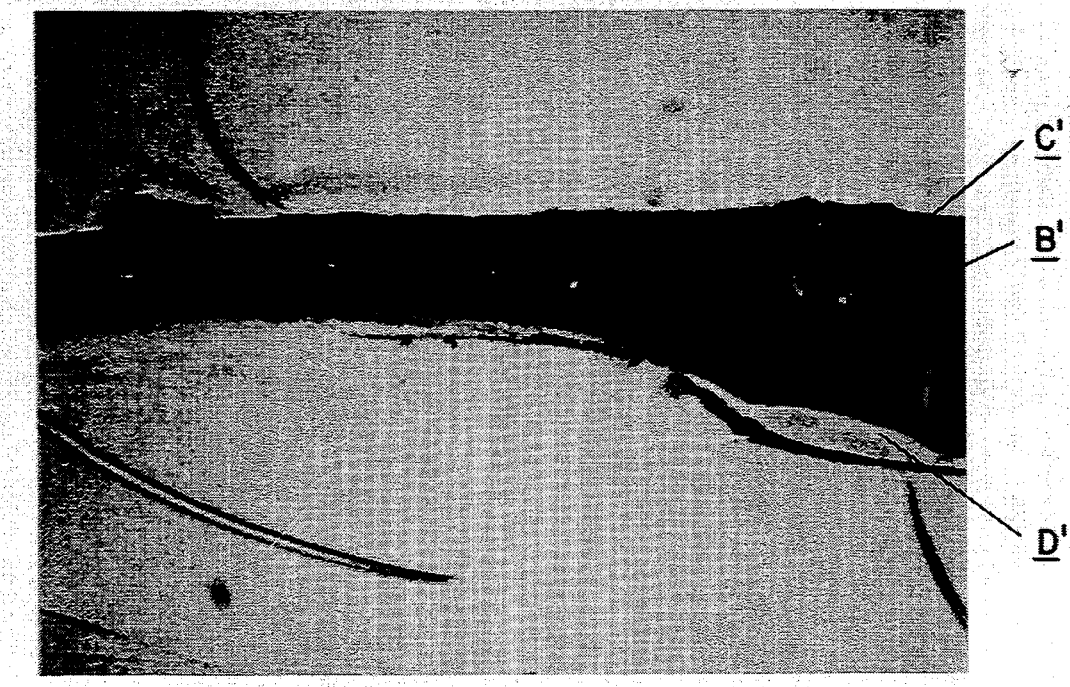

One hundred microliters of the osteogenic solution (protein concentration =1.0 mg/ml in dilute hydrochloric acid) is injected using a 23 gauge needle onto rat calvaria. The subperiosteal injection is localized medial to the mid-sagittal suture line. At ten and fourteen days following the injection, the calvaria are harvested and the tissue is processed for histology by placing the sample into increasing concentrations of ethanol followed by infiltration and embedding in polymethylmethacrylate. Once polymerized, the samples are cut on a diamond saw and milled to a thickness of 30–50 micrometer on a Reichert-Jung Polycut F ultramiller. The sections are stained with Stevenel's Blue and counterstained with Van Gieson pricro-fuchsin and compared qualitatively to tissues obtained from sham injected animals, i.e. injected with just HCl solution. Examination of one of the histological sections (FIG. 1) obtained from animals injected with the osteogenic composition shows that an entire new layer A of trabecular bone has been induced to form which is superimposed on top of the old bone B. This new layer A of woven bone is thicker than the original layer of cortical bone. In contrast, no new bone was generated in one of the tissue sections injected with the control composition, i.e. just HCl alone, as shown in FIG. 2. Reference character B' denotes the old bone in FIG. 2, while reference characters C and C' denote the periosteum and reference characters D and denote the endocranium in FIGS. 1 and 2 respectively.

EXAMPLE 3

A. Preparation of Allograft Tissue

Allograft tissue of the intercalary graft type is etched with a laser to improve the tissue for receiving the osteogenic composition of the invention. Laser beams are irradiated onto a surface of the allograft tissue to etch holes in the tissue of about 500 microns in size and separated by about 1 mm. from each other. These holes are introduced only in the region of the graft where the graft-host junction will be located.

B. Application of Osteogenic Composition

After multiple holes of about 500 microns in size have been etched in the allograft tissue, the osteogenic composition prepared in step (B) of Example 1 is applied into these holes.

EXAMPLE 4

The osteogenic composition prepared in step (B) of Example 1 is subsequently added to a carboxymethylcellulose carrier to produce a gel having about 10% by weight of said osteogenic preparation therein. Similar gels of the same concentration are also produced with respective methylcellulose and hydroxypropyl cellulose carriers.

What is claimed is:

1. A method for preparing an osteogenic composition comprising:
   a) demineralizing bone tissue to provide an acid insoluble demineralized bone matrix from which at least a substantial portion of original calcium content of the bone tissue has been removed, said matrix being made up of collagenous residue and noncollagenous proteinaceous matter;
   b) subjecting the demineralized bone matrix to acid-promoted cleavage of intra-molecular bonds in collagen molecules and inter-molecular bonds between collagen molecules to provide a cleavage product; and
   c) heating the cleavage product to provide a liquid surface-adherent osteogenic composition which is acid soluble upon said heating thereof.

2. The method of claim 1 wherein an osteogenic composition in viscous liquid form is provided.

3. The method of claim 1 wherein in step (b), the demineralized bone matrix is converted to a pulp.

4. The method of claim 1 wherein the demineralized bone matrix contains not greater than about 10 weight percent calcium.

5. The method of claim 3 wherein the demineralized bone matrix contains not greater than about 1 percent calcium.

6. The method of claim 5 wherein the demineralized bone matrix contains not greater than about 0.5 weight percent calcium.

7. The method of claim 1 wherein said heating step (c) is carried out at a temperature of from about 30° to 75° C.

8. The method of claim 7 wherein said heating step (c) is carried out at a temperature of from about 35° to about 60° C.

9. The method of claim 8 wherein said heating step (c) is carried out at a temperature of from about 40° to about 55° C.

10. The method of claim 1 wherein said heating step (c) is carried out for a period of from about 5 minutes to about 10 hours.

11. The method of claim 1 comprising the additional step of
adding demineralized bone powder to said osteogenic composition.

12. The method of claim 1 comprising the additional step of
adding to said osteogenic composition, at least one ingredient selected from the group consisting of antiviral agent, antimicrobial agent, antibiotic agent, amino acid, peptide, vitamin, inorganic element, hormone, endocrine, tissue, synthesizer, enzyme, polymer-cell scaffolding agent with parenchymal cells, angiogenic drug, polymeric drug carrier, collagen lattice, antigenic agent, cytoskeletal agent, cartilage fragment, living cell, natural extract, tissue transplant, bioadhesive, biologically active component, mesenchymal agent, bone digester, antitumor agent, cellular attractant, cellular attachment agent, immunosuppressant, nucleic acid and penetration enhancer.

13. The method of claim 1 comprising the additional step of
applying the osteogenic composition to a surface of a surgical implant device such that the osteogenic composition adheres thereto.

14. The method of claim 13 wherein the surgical implant device is selected from the group consisting of donor bone tissue, an osteoprosthetic device, an orthopedic fracture wrapping and a collagen-coated microspherical filler.

15. The method of claim 1 additionally comprising the step of:
d) treating the liquid composition produced in step (c) to obtain the osteogenic composition in solid form by adding organic solvent to the liquid composition, whereby the osteogenic composition precipitates out of solution in solid form.

16. The method of claim 15 additionally comprising the step of:
titrating the liquid composition produced in step (c), before carrying out step (d), to remove excess acid.

17. The osteogenic composition of claim 15, additionally comprising the step of:
further dissolving the precipitated solid composition from step (d) in solution, whereby the osteogenic composition is in injectable form.

18. The method of claim 17 wherein the osteogenic composition is provided in a form selected from the group consisting of a form suitable for delivery by percutaneous injection to a fracture delivery site, a form for direct injection into an osseous defect resulting from periodontal disease, and as a general injectable substance for stimulating bone growth to counteract bone loss due to injury or disease.

19. The method of claim 1 additionally comprising the step of
d) treating the liquid composition produced in step (c) to obtain the osteogenic composition in solid form, by first titrating the liquid composition produced in step (c) to remove excess acid, then placing the titrated composition in a dialysis bag and then carrying out dialysis, whereby the osteogenic composition remains in the dialysis bag in solid form.

20. The method of claim 19 additionally comprising the step of
further dissolving the osteogenic composition from step (d) in solution, whereby the osteogenic composition is in injectable form.

21. The method of claim 20 wherein the osteogenic composition is provided in a form selected from the group consisting of a form suitable for delivery by percutaneous injection to a fracture delivery site, a form for direct injection into an osseous defect resulting from periodontal disease, and as a general injectable substance for stimulating bone growth to counteract bone loss due to injury or disease.

22. The method of claim 1 wherein said acid-promoted cleavage step (b) is carried out simultaneously with said bone demineralizing step (a).

23. The method of claim 1 wherein said acid-promoted cleavage step (b) is separately carried out after said demineralizing step (a) has been completed.

24. The method of claim 1 wherein said heating step (c) is carried out simultaneously with or subsequent to said acid-promoted cleavage step (b).

25. The method of claim 1 comprising the additional step of
adding hydroxyapatite to the osteogenic composition.

26. The method of claim 1 comprising the additional step of
adding non-demineralized bone powder to the osteogenic composition.

27. The method of claim 1 comprising the additional step of
adding to the osteogenic composition, at least one ingredient selected from the group consisting of bone morphogenic agents and growth factors.

28. The method of claim 27 comprising the additional step of
adding to the osteogenic composition, at least one ingredient selected from the group consisting of platelet derived growth factor, basic fibroblast growth factor, transforming growth factor beta, insulin-like growth factor, and epidermal growth factor.

29. The method of claim 1 comprising the additional step of incorporating the osteogenic composition within a surgical implant device.

30. The method of claim 29 wherein the surgical implant device is selected from the group consisting of donor bone tissue, an osteoprosthetic device, an orthopedic fracture wrapping and a collagen-coated microspherical filler.

31. The method of claim 1 wherein the demineralized bone tissue is derived from the group consisting of cortical autogenic, cortical allogeneic, cortical xenogeneic, cancellous autogenic, cancellous allogeneic, cancellous xenogeneic, corticocancellous autogenic, corticocancellous allogeneic and corticocancellous xenogeneic bone.

32. The method of claim 1 wherein concentration of acid in step (b) is at least about 2.0N.

* * * * *